(12) United States Patent
Kim et al.

(10) Patent No.: US 7,374,776 B2
(45) Date of Patent: May 20, 2008

(54) BONE-FILLING COMPOSITION FOR STIMULATING BONE-FORMING AND BONE-CONSOLIDATION COMPRISING CALCIUM SULFATE AND VISCOUS BIOPOLYMERS

(75) Inventors: In-San Kim, Taegu (KR); Byung Chae Cho, Taegu (KR)

(73) Assignee: Regen Biotech, Inc. (KR)

( * ) Notice: Subject to any disclaimer, the term of this patent is extended or adjusted under 35 U.S.C. 154(b) by 0 days.

(21) Appl. No.: 10/528,749

(22) PCT Filed: Sep. 30, 2002

(86) PCT No.: PCT/KR02/01839

§ 371 (c)(1),
(2), (4) Date: Mar. 22, 2005

(87) PCT Pub. No.: WO2004/028580

PCT Pub. Date: Apr. 8, 2004

(65) Prior Publication Data

US 2006/0165799 A1    Jul. 27, 2006

(51) Int. Cl.
*A61F 2/00* (2006.01)
*A61K 33/42* (2006.01)
*A61K 33/00* (2006.01)
*A61K 33/10* (2006.01)
*A61K 33/06* (2006.01)
*A61K 47/00* (2006.01)
*A01N 59/26* (2006.01)
*A01N 59/24* (2006.01)
*A01N 59/06* (2006.01)
*A01N 25/00* (2006.01)

(52) U.S. Cl. .................. 424/426; 424/423; 424/602; 424/611; 424/686; 424/687; 424/696; 424/715; 514/781; 514/784

(58) Field of Classification Search .............. 424/423, 424/426, 602, 611, 686, 687, 696, 715; 514/781, 514/784
See application file for complete search history.

(56) References Cited

U.S. PATENT DOCUMENTS

| 4,795,475 A | * | 1/1989 | Walker ................... 128/898 |
| 5,281,265 A | * | 1/1994 | Liu ........................ 106/35 |
| 6,030,635 A | | 2/2000 | Gertzman et al. |
| 6,458,375 B1 | | 10/2002 | Gertzman et al. |
| 6,692,563 B2 | * | 2/2004 | Zimmermann .......... 106/696 |
| 2002/0071827 A1 | * | 6/2002 | Petersen et al. ......... 424/93.1 |

OTHER PUBLICATIONS

Webster's II New College Dictionary 1999 p. 111.*
Cho et al. J. Craniofac. Surg. 2002, 13(3), 465-75.*
Gabriele Pecora, et al., Bone Regeneration With a Calcium Sulfate Barrier, Oral Surgery Oral Medicine Oral Pathology, vol. 84, pp. 424-429, 1997.
Gavriil A. Ilizarov, et al., The Tension-Stress Effect on the Genesis and Growth of Tissues: . . . , Clinical Orthopaodics, vol. 539, pp. 263-285, 1989.
Jeffrey Fischgrund, M.D., et al., Variables Affecting Time to Bone Healing During Limb Lengthening, Clinical Orthopaedics and Related Research, No. 301, pp. 31-37, 1994.
Fred Flandry, M.D., et al., The Effect of the Cat-Cam Above-Knee Prosthesis on Functional Rehabilitation, Clinical Orthopaodics, No. 239, pp. 249-262, 1989.
William H. Beeson, MD, Plaster of Paris as an Alloplastic Implant in the Frontal Sinus, Arch Otolaryngol, vol. 107, 1981.

* cited by examiner

*Primary Examiner*—Sreeni Padmanabhan
*Assistant Examiner*—Ernst V Arnold
(74) *Attorney, Agent, or Firm*—Lucas & Mercanti, LLP (57) ABSTRACT

The present invention relates to a composition for bone-filling, more particularly, to a bone-filling composition for stimulating bone-formation and bone consolidation comprising calcium sulfate and viscous biopolymers. The composition of the present invention can easily be administered into the missing part of injured bone. Since the composition of the present invention does not diffuse to surrounding organs, it can effectively be used for bone-filling material suitable for body.

6 Claims, 14 Drawing Sheets

BONE-FILLING COMPOSITION FOR STIMULATING BONE-FORMING AND BONE-CONSOLIDATION COMPRISING CALCIUM SULFATE AND VISCOUS BIOPOLYMERS

This patent application claims the benefit of priority from PCT Application Ser. No. PCT/KR2002/001839 filed Sep. 30, 2002, the contents of which are incorporated herein by reference.

FIELD OF THE INVENTION

The present invention relates to a composition for bone-filling, more particularly, to a bone-filling composition for stimulating bone-formation and bone-consolidation comprising calcium sulfate and viscous biopolymers, and a use thereof for stimulating bone-formation and bone-consolidation.

BACKGROUND ART OF THE INVENTION

Recently, bone-loss is often caused by a disease or a car accident, so that supplementing bone-loss is importantly required. Bone-transplantation is one way to supplement bone-loss and more preferably bone-filling composition is used. Bone-extension technique is performed today to extend one's height in stature or to correct undersized jaws, for which bone-filling composition is also required a lot.

Bone-extension technique is to stimulate bone-growth, especially growth in height, by stretching based on the theory that "Tension forces stimulate histogenesis". Bone-extension technique was first devised for the growth of limb bones but has been widely used for jawbone extension. Jawbone extension method is one of techniques performed in the field of cranial jaw facial surgery, which can improve facial ratio not by cutting bone but by moving facial bones gradually by fixing bone-stretching apparatus to retreated parts of jawbone and central facial form.

Bone-extension technique has been successfully used for supplementing the loss of long bone since Ilizarov found out biomechanical elements for bone-extension (Ilizarov G A, *J. Dis. Orthop. Inst.*, 48(1): 1, 1988; Ilizarov G A, *Clin. Ortho.*, 239: 263, 1989; Ilizarov G A, *Clin. Ortho.*, 238: 249, 1989) . It is important for performing the successful bone-extension to keep blood circulation in the part of bone-extension and to fix external fixator stably to both sides of joint part of cortical bone, resulting in the stimulation of bone-consolidation by gradual extension of bone (White S H, *J. Bone Join Surgery,* 72-B: 350, 1990; White S H, *Orthop. Clin. North. Amer.,* 22: 569, 1991; Fishgrund J., Paley D., Sulter D., *Clin. Orthop.,* 301: 31, 1994).

The period of bone-consolidation depends on extension part of bones such as facial bone or long bone, blood circulation condition, the age of a patient, etc. Bone-consolidation of craniofacial bone takes 3-5 weeks for children and 6-12 weeks for adults after bone-extension, while it takes 3-6 months in long bone regardless of age. Performing bone-extension for craniofacial bone has a couple of problems; one is carrying high possibility of complications and the other is postponing the return to normal life due to the long bone-consolidation time. Precisely, the treatment after bone-extension takes 2-4 months composing of latent phase, bone-extension phase and bon-consolidation phase.

According to Charls and Sailer's report, extending 1 mm a day shows stronger biochemical and physiological characteristics than extending 2-3 mm a day (Carls & Sailer, *J. Craniomaxillofac Surg.,* 94: 152, 1994). Ilizarov has also reported that extending 1 a day showed best results while extending 0.5 mm a day caused premature bone-consolidation and extending 2 mm a day caused undesirable changes in extended tissues (Ilizarov, *J. Dis. Orthop. Inst.,* 48(1): 1, 1988; Ilizarov, *Clin. Ortho* 239: 263, 1989). In addition, it has also been known that consecutive extending causes the least damage in tissues but the best development of capillary vessels and bone-formation. Therefore, shortening the period of bone-extension and bone-consolidation can contribute to prevent possible complications and to make a patient return to normal life early. In order to shorten the period of bone-extension and bone-consolidation, bone-filling composition is used to stimulate bone-formation and bone-consolidation.

Meanwhile, autobone-graft, treated homograft, heterograft and bone graft substitute have been known to stimulate bone-formation. Autobone-graft is used for the treatment of joint-agglutination or non-agglutinational fracture, or for avoiding damage and void caused by infection, tumor and operation by supplementing bone cavity or bone loss. Transplanted autobone is adsorbed well, resulting in re-circulation of blood. At this time, osteoprogenitor cells are differentiated to bony osteogenesis cells and the activation thereof stimulates bone-regeneration as well as treats bone-loss. However, autobone-graft has problems such as limitation in the amount of extraction and high morbidity caused by the secondary operation for the part of donation. Thus, bone morphogenic protein or other bone-grafting substitute is used to induce bone-regeneration at extended sites. Bone morphogenic protein is regarded as the strongest bone-inducing material but is limited in clinical use because it is very expensive and hard to obtain.

Calcium sulfate is a kind of bone-filling material that is suitable for human body and induces the growth of bony osteogenesis cells and blood vessels as well as stimulates bone-consolidation in the early stage. This material is contribute to construct a normal bone structure by stimulating new bone-formation in a proper condition, plays as a defense shield during bone-healing by preventing the growth of unnecessary connecting tissues and can be substituted with bone during the recovery process. Beeson confirmed by the experiment with dogs that calcium sulfate injected into frontal sinus of dogs induced bone-regeneration within 4-6 weeks (Beeson W., *Arch Otolaryngol,* 107: 664, 1981), and Pecora et al. also reported bone-healing effect of calcium sulfate injected into bone-loss area of mouse jawbone that was observed partly or over the whole area three weeks after injection (Pecora G., Andreana S., Margarone III J E., Covani U., Sottosanti J S., *Oral Surg. Oral Med. Oral Pathol. Oral Radio Endod.,* 84: 434, 1997). According to Pelter's report, calcium sulfate was safe to be administered to various types of bone-loss patients, stimulated bone-regeneration as being absorbed in a body within several weeks or several months and did not cause any complication or any danger (Pelter L F., *Am. J. Surg.,* 97(3): 311, 1959). However, the conventional calcium sulfate used as a bone-filling composition for bone-regeneration is difficult to be injected in bone-loss area because the composition is in a form of tablets or powder. In order to inject that composition, operation with a scar is unavoidable, which suffers patients.

Thus, the present inventors have tried to improve the way to administer calcium sulfate. As a result, the present inventors prepared a gel type composition containing calcium sulfate and viscous polymer, and accomplished the present invention by confirming that the composition of the invention can easily be administered into the bone-loss area by injection, does not diffuse to surrounding organs and shortens the bone-consolidation period by stimulating bone-formation and bone-consolidation.

SUMMARY OF THE INVENTION

It is an object of the present invention to provide a gel type bone-filling composition stimulating bone-formation and bone-consolidation that is easily administered into the missing part of injured bone and stays longer in that area.

BRIEF DESCRIPTION OF THE DRAWINGS

A: osteoblasts B: fibrous tissues

DETAILED DESCRIPTION OF THE INVENTION

To achieve the above object, the present invention provides a gel type composition for bone-filling comprising calcium sulfate and viscous biopolymer.

The present invention also provides a use thereof for stimulating bone-formation and bone-consolidation.

Further features of the present invention will appear hereinafter.

The present invention provides a gel type composition for bone-filling comprising calcium sulfate and viscous biopolymer.

The composition of the present invention consists of
a) mixture (20~80 weight %) consisting of $CaSO_4$ (90~99 weight %) and $CaCO_3$, $MgCO_3$ and $CaCO_3.MgCO_3$ (1~10 weight %); and
b) viscous biopolymer (80~20%)

$CaSO_4$ is the chief ingredient of the composition of the present invention and one or more inorganic salts selected from a group consisting of $CaCO_3$, $MgCO_3$, $CaCO_3.MgCO_3$ and the mixture of them can be added to the composition. In the preferred embodiments of the present invention, it is preferable that $CaSO_4$ takes 90~99 weight % of the total weight of inorganic salts and $CaCO_3$, $MgCO_3$, $CaCO_3.MgCO_3$ take 1~10 weight %. It is more preferable that $CaSO_4$ takes 98~99 weight %, $CaCO_3$ does 0.3~1 weight %, $MgCO_3$ does 0.3~1 weight % and $CaCO_3.MgCO_3$ does 0.5~1 weight % for the total weight of the composition. Calcium sulfate is a less expensive bone-filling material and generally provided as a highly purified powder or pills (see FIG. 1). When calcium sulfate is absorbed in bone, newly forming bone recovers anatomical and structural characteristics, resulting in the acceleration of the new bone growth. In addition, calcium sulfate is absorbable and comparatively safe material without any inflammatory reaction.

In this invention, a gel type composition was prepared by mixing powder type calcium sulfate and viscous biopolymer. The viscous biopolymer can be selected from a group consisting of carboxymethylcellulose, hyaluronic acid, chitosan, polyacrylic acids, polyvinyl ethers, polystyrenes, cellulose ethers, cellulose esters, starches and polysaccharides. In the preferred embodiment of the present invention, carboxymethylcellulose was used as a viscous biopolymer.

The preferable proportion of powder type calcium sulfate to viscous biopolymer for the composition of the present invention is 20:80~80:20, and the ratio of 50:50 is more preferable.

In the preferred embodiment to prepare the gel type composition of the present invention, sodium salt of polycarboxymethyl ether of cellulose can be used for carboxymethylcellulose used as a viscous biopolymer. The carboxymethylcellulose sodium salt is an odorless hydroscopic powder having various colors such as white, cream color, etc and is used for a base material. This material is used in the form of suspension or milky liquid.

Carboxymethylcellulose is also known to be a harmless protecting material used for ileostomy or colostomy (Raynolds J E F., Martindale., *The Extra Pharmacopoeia.*, 29: 1433, 1989).

The present inventors injected the mixture of calcium sulfate and viscous biopolymer into the extended area using 18-gauge needle, which was easy and time saving method not requiring secondary operation. The composition of the present invention stimulated new bone-formation by powerful mineralization 3 weeks after injection and the new bone-formation was widely observed 6 weeks after injection. In addition, the above composition was slowly absorbed in a body after injection and finally only calcium sulfate that did not affect bone-regeneration was left during which inflammatory reaction was not caused. Thus, the composition of the present invention was confirmed to be a safe material.

The present invention also provides a use of the composition for stimulating bone-formation and bone-consolidation.

In order to confirm if the composition for bone-filling can stimulate bone-formation and bone-consolidation, the present inventors performed bone-extension at jawbone of a dog 2 mm or 1 mm per day, after which the present inventors injected the composition thereto and investigated the effect of the composition on bone-consolidation in the early stage.

As a result, it was observed that the calcification was undergoing around the extended area of jawbone in every group in which extension was induced 2 mm per day except control group, which was confirmed by radiographs taken in the $3^{rd}$ week and in the $6^{th}$ week after extension. Radiolucent zone was also observed between extended jawbone spicules and consolidated areas abutting on the both sides of jawbone spicules were all different group by group. In $3^{rd}$ week after bone-extension, radiodense zone was hardly observed in a control group in which bone-extension was induced 1 mm or 2 mm per day without injection of the composition, so was in another group in which bone extension was performed 2 mm per day with injection of the composition while huge radiodense zone was observed in the group in which bone-extension was induced 1 mm per day with the injection of the composition. In $6^{th}$ week after bone-extension, radiodense zone was gradually stretching to the center of extended area both in a control group in which bone-extension was induced 1 mm per day without injection of the composition and a group in which bone-extension was induced 1 mm or 2 mm per day with the injection of the composition. The largest radiodense zone was observed in the group in which bone-extension was induced 1 mm per day with the injection of the composition while radiodense zone was hardly seen in the control group in which bone-extension was induced 2 mm per day without the injection of the composition (see FIG. 3-FIG. 5).

Histological test was also performed. As a result, osteoblasts forming osteoid were observed around the edge of extended area and many fibrous tissues were also observed in the center of the extended area in a control group in which bone-extension was induced 1 mm per day without the composition in the $3^{rd}$ week after extension (see FIG. 6A). The new bone-formation became larger in that group in $6^{th}$ week after extension, though the center of the extended area was filled with fibrous tissues (see FIGS. 6B and 6C). In another control group in which bone-extension was induced 2 mm per day without the injection of the composition, new bone was partly observed in the extended area and most of the extended area was filled with fibrous tissues (see FIG. 7).

Figure 8A:
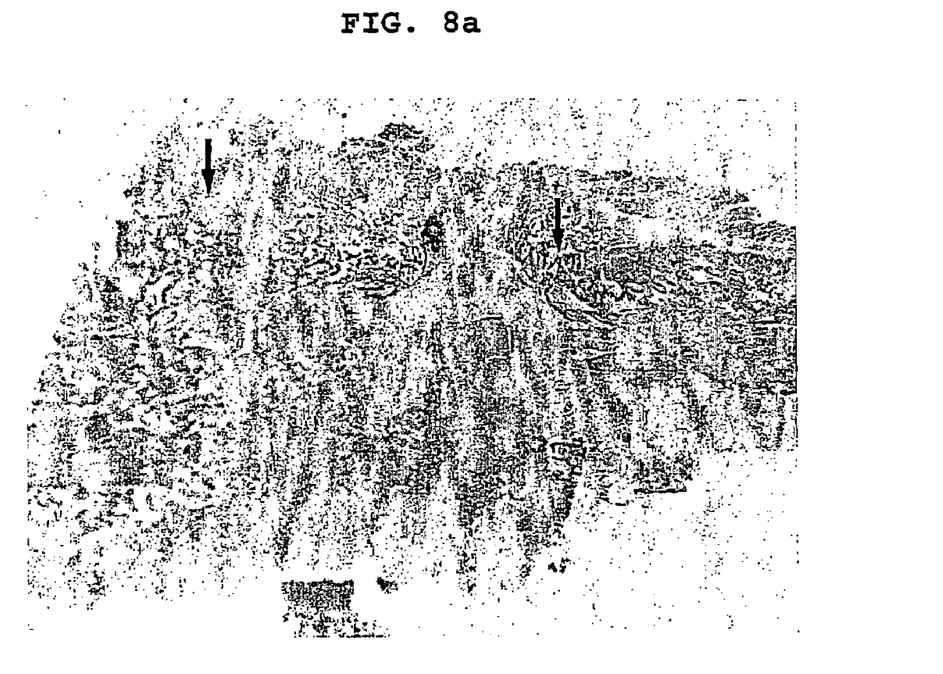
FIG. 8A is a photograph showing the histological section of a calcium sulfate group 1 3 weeks after bone extension, particularly the group was injected with the composition of the present invention and was induced to have 1 mm extension per day for 10 days, Arrows: the first cutting parts
Figure 8B:
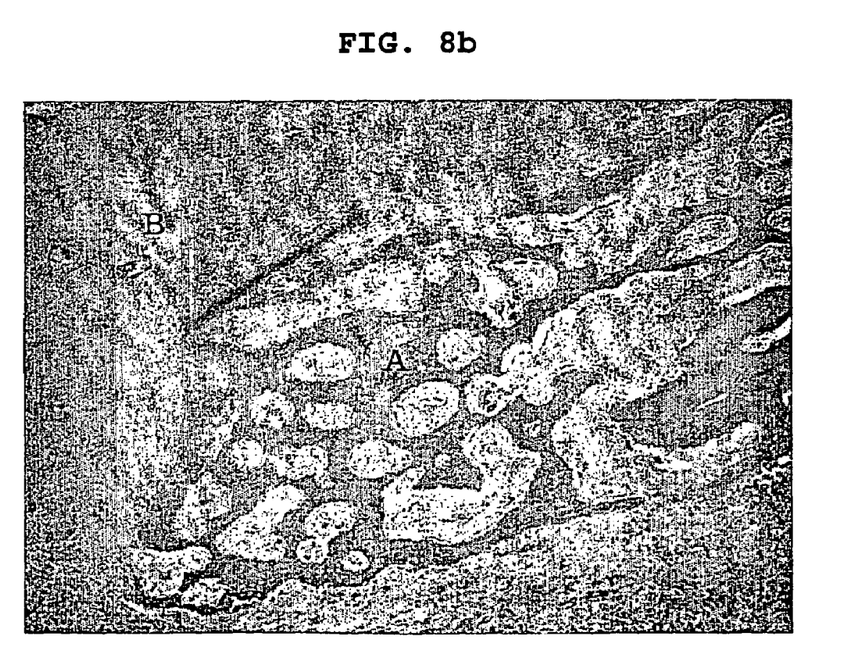
FIG. 8B is a photograph showing that the center of the extended region was filled with osteoblasts and fibrous tissues, which was confirmed by hematoxylin & eosin staining with the histological section of FIG. 8A, A: osteoblasts B: fibrous tissues

In the meantime, lots of active osteoblasts were observed from the edge to the center of the extended area and newly formed bone and fibrous tissues were dominant in a group in which bone-extension was induced 1 mm per day with the injection of the composition in $3^{rd}$ week after extension (see FIGS. 8A and 8B). The generated new bones were distributed all over the extended area just like normal cortical bones in that group in $6^{th}$ week after extension (see FIGS. 8C and 8D). The extended area of the group in which bone-extension was induced 2 mm per day with the injection of the composition was connected with fibrous interzone and bone-formation around the edge was observed in $3^{rd}$ week after extension (see FIGS. 9A and 9B). Bone-formation was observed in half of the extended area in that group in $6^{th}$ week after extension (see FIGS. 9C and 9D).

As described hereinbefore, less bone-formation was observed in the group in which bone-extension was induced 2 mm per day with the injection of the composition, comparing to the group in which bone-extension was induced 1 mm per day with the injection of the composition. Thus, 1 mm extension per day is believed to be clinically more effective.

In the control group in which bone-extension was induced 1 mm per day without the injection of the composition, the extended area was not replaced with newly formed bone until the $6^{th}$ week after extension and most of the extended area was filled with fibrous tissues except the edge on which partial bone-formation began. Taking the above results and the reports of Califano and Komuro into consideration (Califano L, Cortese A, Zupi A, Tajana G, *J. Oral Maxillofac. Surg.*, 1994, 52, 1179; Komuro Y, Takato T, Harii K, Yonemara Y, *Plast. Reconstr. Surg.*, 1994, 94, 152), bone-consolidation takes at least 6 weeks and the faster the extension speed is, the shorter the bone-extension period is. Fast extension is, thus, preferable as long as it does not disturb bone-formation since it can relieve suffering and prevent complications after operation by shortening bone-consolidation period.

Generally, extended bone tends to be absorbed, so that 10-20% over-extension is preferable. The accurate result of the over-extension was not reported, though. So, the extent of over-extension was decided by operator's experience. The adsorption of extended bone seems to depend on mineralization of the extended bone. As for an adult or an aged patient, it is required to wait 6-10 weeks after bone-extension for complete bone-consolidation. However, the present inventors believe that over-extension is not necessary if the composition of the present invention is used since the composition stimulates bone-regeneration From the above results, it is confirmed that the composition of the present invention can be effectively used as an economical bone-filling composition suitable for body because the composition stimulates bone-formation and bone-consolidation in the early stage after bone-extension, leading to the shortening the bone-consolidation period.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of Composition for Bone-Filling

The present inventors have prepared a composition for bone-filling by mixing carboxymethylcellulose (referred as "CMC" hereinafter) with calcium sulfate. Particularly, mixed 98.9 g of $CaSO_4.H_2O$, 0.3 g of $CaCO_3$, 0.3 g of $MgCO_3$ and 0.5 g of $CaCO_3.MgCO_3$ together, added thereof to 100 g of CMC and, then suspended thereof well, resulting in the preparation of a gel type composition of the present invention.

Example 2~Example 7

Based on the ratio presented in the below Table 1, the present inventors prepared gel type compositions with the same method as the above Example 1.

TABLE 1

Composition ratio

| | $CaSO_4 \cdot H_2O$ | $CaCO_3$ | $MgCO_3$ | $CaCO_3 \cdot MgCO_3$ | Ratio to CMC |
|---|---|---|---|---|---|
| Example 2 | 98 g | 0.5 g | 0.5 g | 1 g | 20:80 |
| Example 3 | 98 g | 0.4 g | 0.4 g | 1.2 g | 30:70 |
| Example 4 | 98.5 g | 0.3 g | 0.2 g | 1 g | 40:60 |
| Example 5 | 98.5 g | 0.5 g | 0.5 g | 0.5 g | 60:40 |
| Example 6 | 99 g | 0.3 g | 0.2 g | 0.5 g | 70:30 |
| Example 7 | 99 g | 0.2 g | 0.5 g | 0.3 g | 80:20 |

Experimental Example 1

Bone-Extension Operation

In order to confirm if the composition of the present invention stimulates bone-formation and bone-consolidation in the early stage of bone-extension, the present inventors performed bone-extension operation at jawbones of dogs. After operation, the inventors injected the composition and then observed any change.

Particularly, selected 8 5-month old dogs for experiment and grouped them by 4 for a control group and for a composition group. Divided those groups into subgroups such as a control group 1 in which bone-extension was induced 1 mm per day, a control group 2 in which bone-extension was induced 2 mm per day, a composition group 1 in which bone-extension was induced 1 mm per day, a composition group 2 in which bone-extension was induced 2 mm per day.

Figure 2:
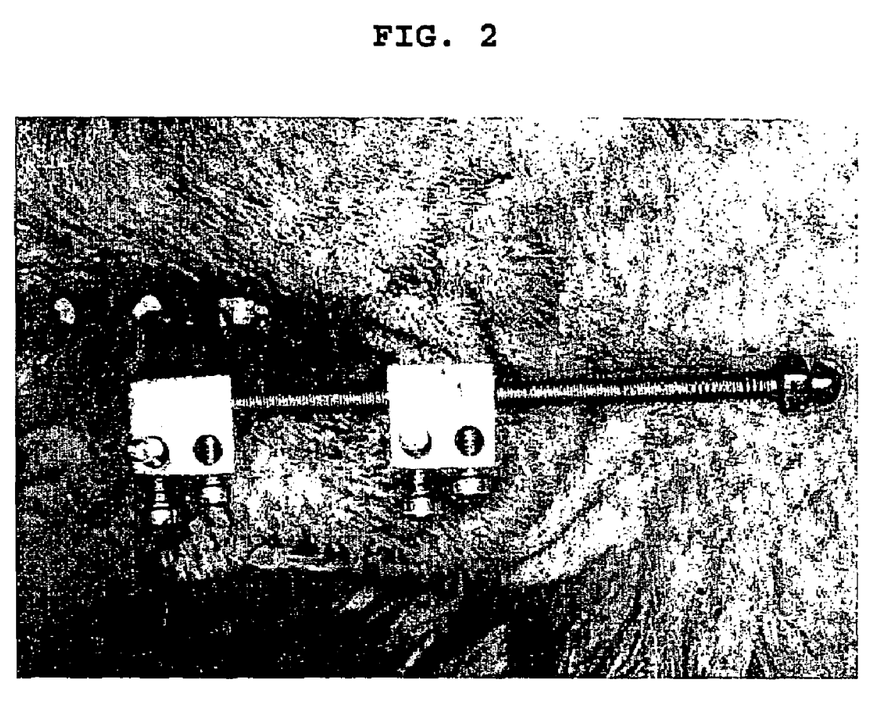
FIG. 2 is a photograph showing the setting of an external fixator to a test animal as performing bone extension operation using the composition of the present invention.
Figure 3A:
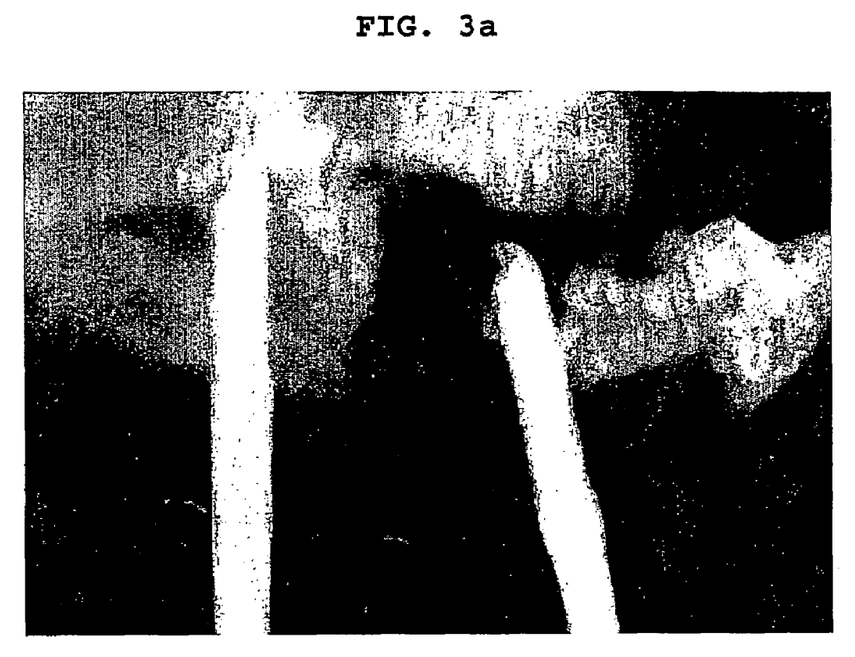
FIG. 3A is a photograph showing the extent of bone-consolidation in a control group 1 that was measured with radio-assay 3 weeks after bone extension, particularly the control group 1 was injected with only carboxymethylcellulose and was induced to have 1 mm extension per day for 10 days.
Figure 3B:
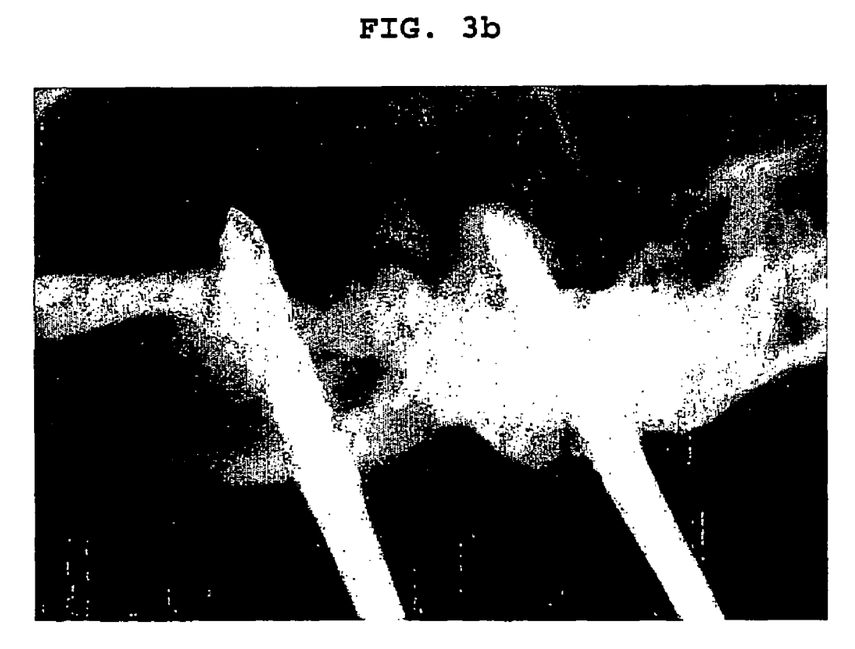
FIG. 3B is a photograph showing the extent of bone-consolidation in a control group 1 that was measured with radio-assay 6 weeks after bone extension, particularly the control group 1 was injected with only carboxymethylcellulose and was induced to have 1 mm extension per day for 10 days.
Figure 3C:
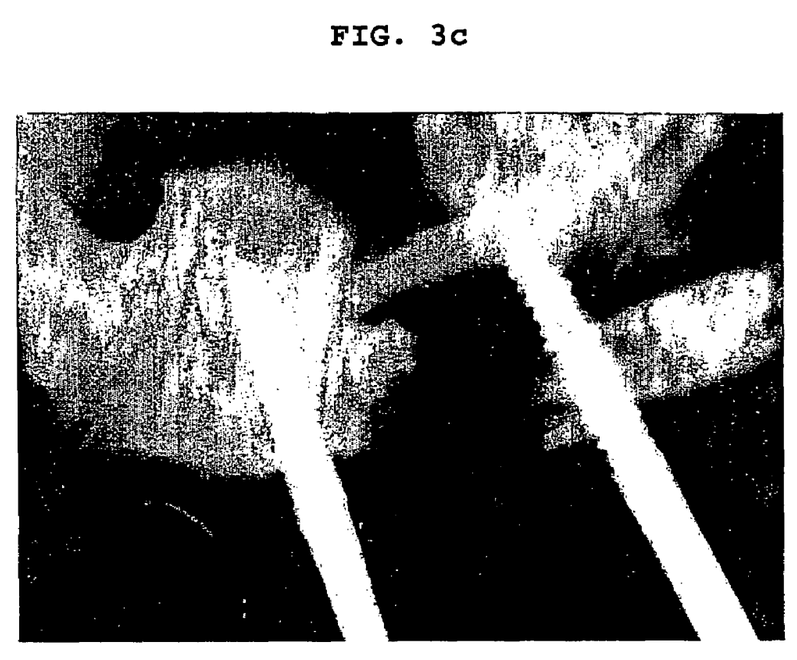
FIG. 3C is a photograph showing the extent of bone-consolidation in a control group 2 that was measured with radio-assay 3 weeks after bone extension, particularly the control group 1 was injected with only carboxymethylcellulose and was induced to have 2 mm extension per day for 5 days.
Figure 3D:
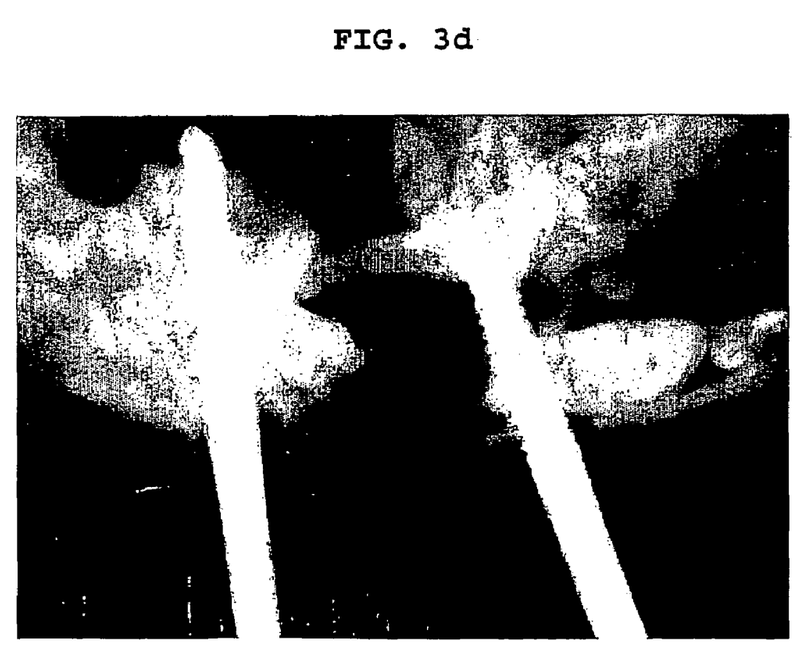
FIG. 3D is a photograph showing the extent of bone-consolidation in a control group 2 that was measured with radio-assay 6 weeks after bone extension, particularly the control group 2 was injected with only carboxymethylcellulose and was induced to have 2 mm extension per day for 5 days.

Kept the breath of dogs through tubes inserted in organs after general anesthesia and shaved the operating part, followed by sterilization and application. Incised skin 3-4 cm along the lower end of jawbone, lifted masseter muscle and exposed the side part of jawbone. Then, performed vertical osteotomy at the trunk of jawbone using an electric saw and completely cut jawbone. Fixed each fixing pin of external fixator on spicule 1 cm away from the cutting area right and left. While fixing the pins on the jawbone spicule with drill, kept washing with saline solution not to burn the fixing sites. Inserted the pins just as deep as it barely passed through jawbone and then fixed them tightly. After fixing two pins all, set them on bone extending apparatus (Molina Distractors, Wells Johnson Company) (FIG. 2).

Sutured the incised area with 5-0 vicryl and 5-0 nylon stitching fiber layer upon layer and recovered the dogs from anesthesia. Administered penicillin (100,000 μ/kg) by intramuscular injection every 12 hours for 7 days after operation and oral-administered anodyne every 4-6 hours to relieve pain. Fed the dogs with soft diet until the second day after operation and provided regular diet from the third day. From the fifth day after operation, started bone-extension 1 mm per day for 10 days (control group 1 and composition group 2) or 2 mm per day for 5 days (up to 10 mm total; control group 2 and composition group 2).

Figure 1:
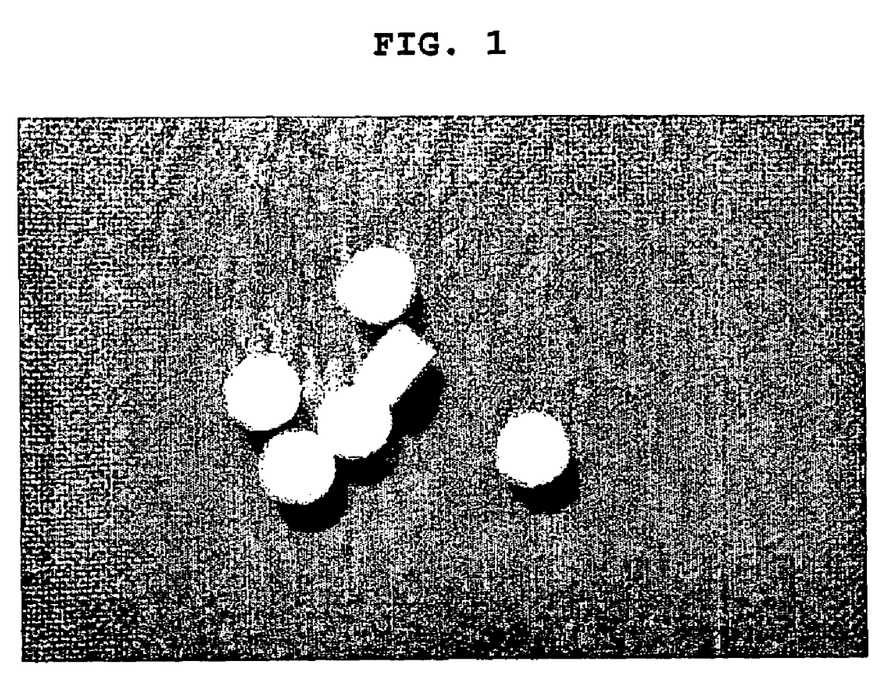
FIG. 1 is a photograph showing the pills of calcium sulfate that are used in the preparation of the composition of the present invention.

On the day when bone-extension was finished, injected 1 ml of the composition for bone-filling prepared in the above Example 1 into the extended area using 18 gauge needle (FIG. 1B). Meanwhile, injected only 1 ml of carboxymethylcellulose into the extended area for control groups.

After the injection of the composition, kept the bone-extension apparatus for 6 weeks to induce bone-consolidation and bone-regeneration. Sacrificed the first 4 dogs selected from each group by one in the $3^{rd}$ week after bone-extension by injecting overdose of pentobarbital (40-50 mg/kg) and so did for the rest 4 dogs in the $6^{th}$ week.

<1-1> Radio-Assay

Examined each animal group went through bone extension with radio-assay every week and observed bone-formation and bone-consolidation through the radiographs taken after 3 weeks and 6 weeks respectively.

Figure 4A:
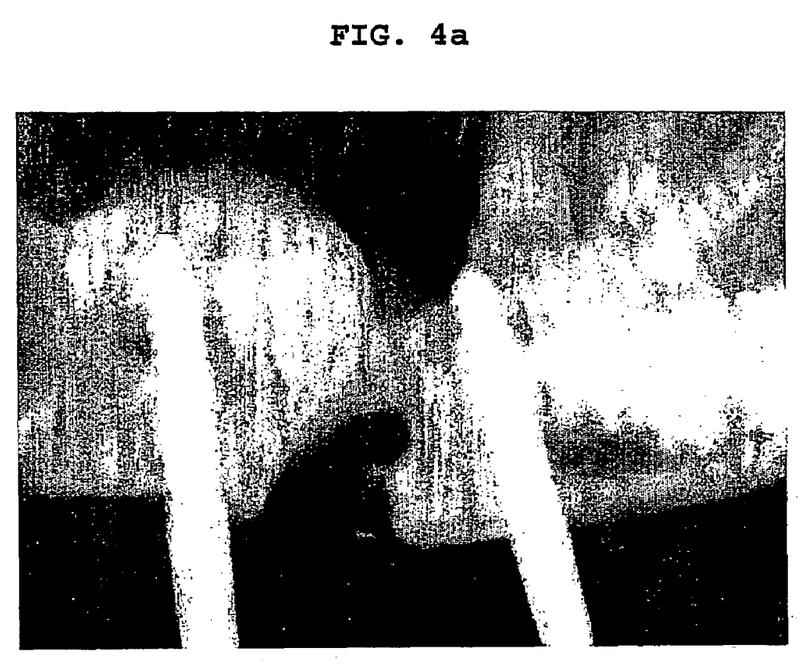
FIG. 4A is a photograph showing the extent of bone-consolidation in a calcium sulfate group 1 that was measured with radio-assay 3 weeks after bone extension, particularly the calcium sulfate group 1 was injected with the composition of the present invention and was induced to have 1 mm extension per day for 10 days.
Figure 4B:
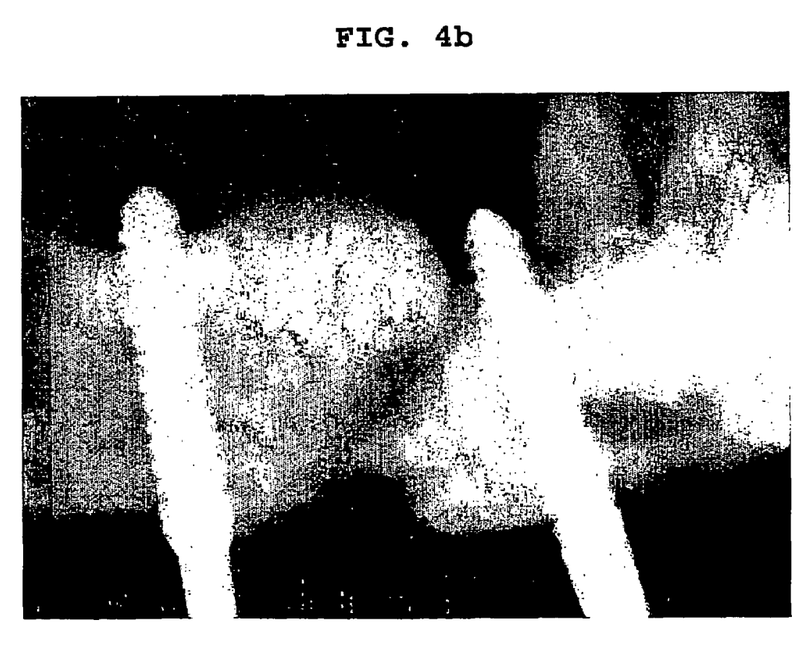
FIG. 4B is a photograph showing the extent of bone-consolidation in a calcium sulfate group 1 that was measured with radio-assay 6 weeks after bone extension, particularly the calcium sulfate group 1 was injected with the composition of the present invention and was induced to have 1 mm extension per day for 10 days.
Figure 5A:
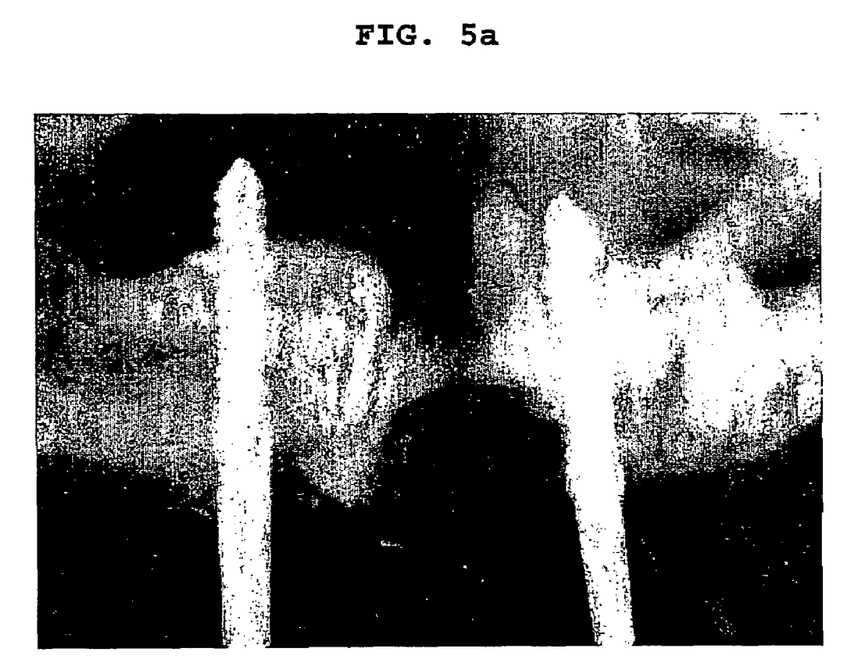
FIG. 5A is a photograph showing the extent of bone-consolidation in a calcium sulfate group 2 that was measured with radio-assay 3 weeks after bone extension, particularly the calcium sulfate group 2 was injected with the composition of the present invention and was induced to have 2 mm extension per day for 5 days.
Figure 5B:
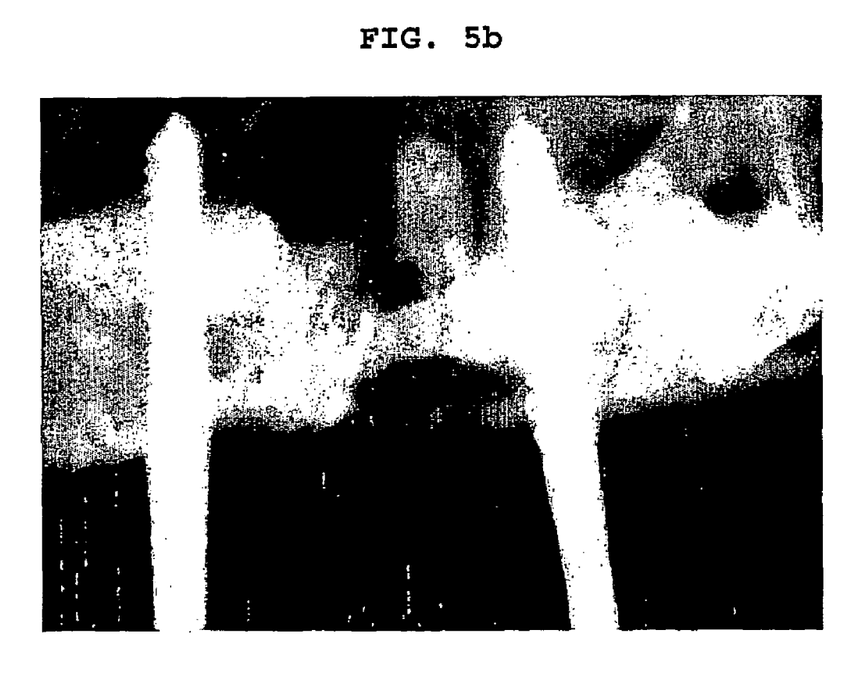
FIG. 5B is a photograph showing the extent of bone-consolidation in a calcium sulfate group 2 that was measured with radio-assay 6 weeks after bone extension, particularly the calcium sulfate group 2 was injected with the composition of the present invention and was induced to have 2 mm extension per day for 5 days.

As a result, observed undergoing calcification in the extended area of jawbone in every group except a control group 2 (FIG. 3-FIG. 5). Confirmed radiolucent zone in between the extended jawbone spicules and other consolidated area abutting on both sides of jawbone spicules. Hardly found radiodense zone in control groups and a composition group 2 in the $3^{rd}$ week after bone-extension while observed a huge radiodense zone in a composition group 1. Confirmed that radiodense zone was stretching toward the center of the extended area in every group except a control group 2 in the $6^{th}$ week after extension, and detected the largest radiodense zone in a composition group 1.

<1-2> Histological Test

Bone samples were taken from extended jawbone including normal osseous tissues therearound with an electric saw. The obtained spicules were fixed in 10% neutral formalin for 1 week, and then decalcified in 10% nitric acid and 10% sodium citrate for 2 days. 4-6 μm of specimens were prepared by dehydration and paraffin-fixation following general techniques. The specimens were stained with hematoxylin-eosin to observe histological changes using an optical microscope.

Figure 6A:
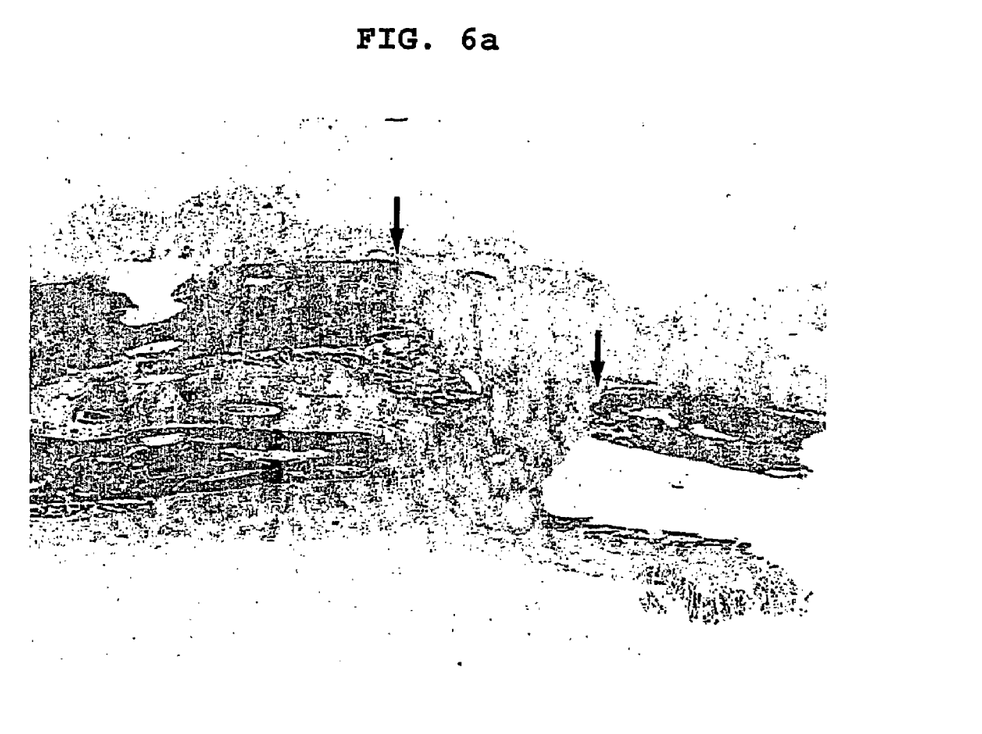
FIG. 6A is a photograph showing the histological section of a control group 1 3 weeks after bone extension, particularly the group was injected with only carboxymethylcellulose and was induced to have 1 mm extension per day for 10 days, Arrows: the first cutting parts
Figure 6B:
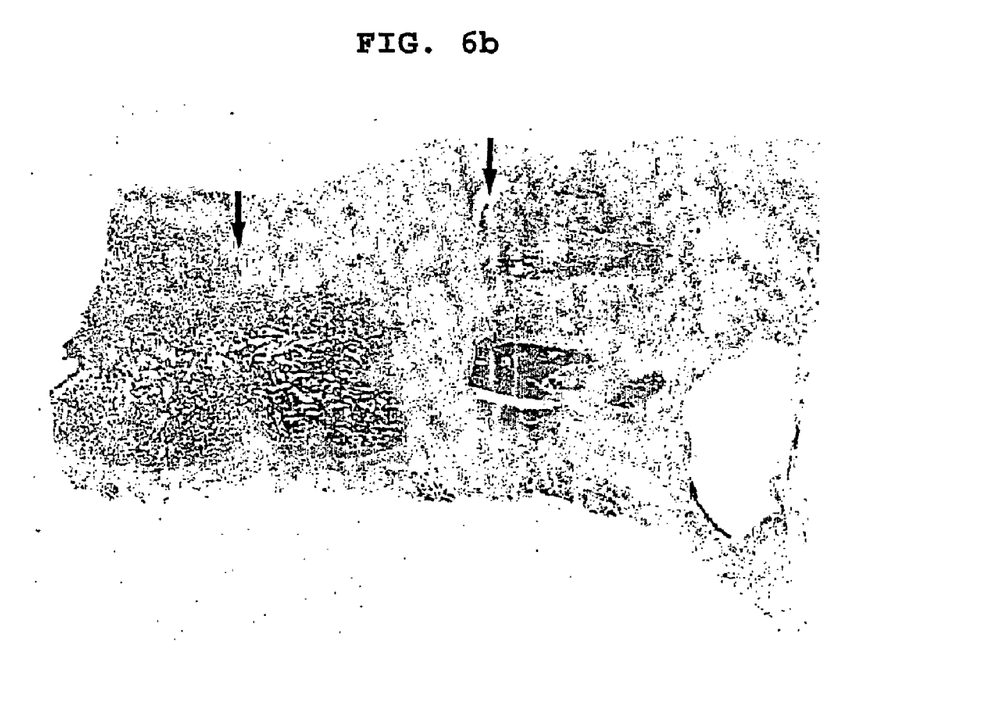
FIG. 6B is a photograph showing the histological section of a control group 1 6 weeks after bone extension, particularly the group was injected with only carboxymethylcellulose and was induced to have 1 mm extension per day for 10 days, Arrows: the first cutting parts
Figure 6C:
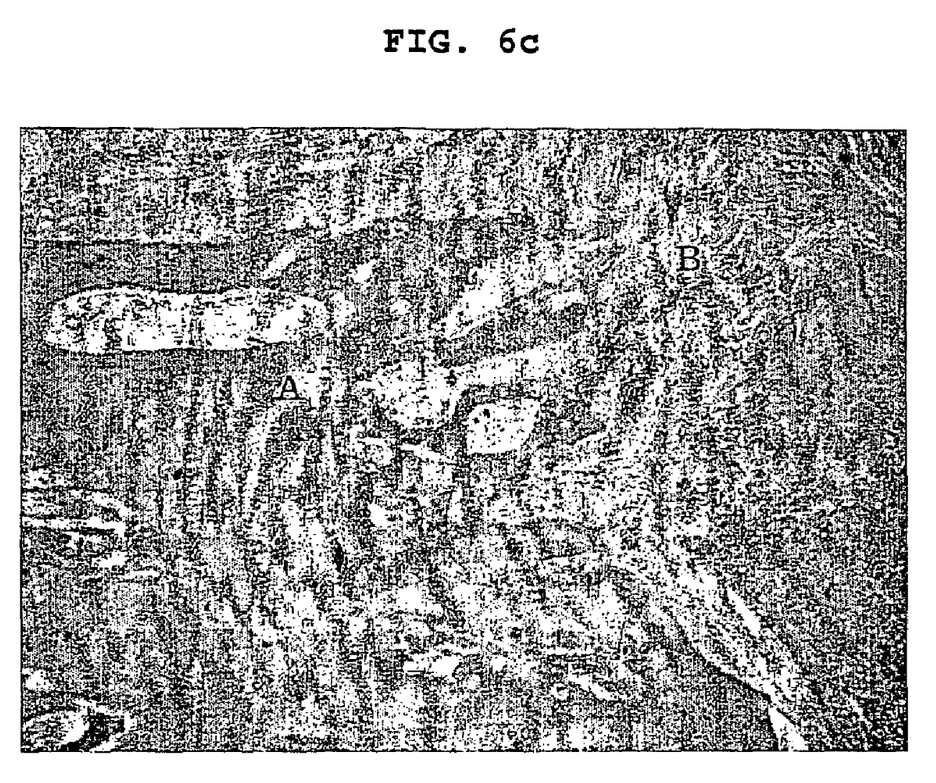
FIG. 6C is a photograph showing the new bone-formation at the edge of bone extension region in a control group 1 injected carboxymethylcellulose only and induced to have 1 mm extension per day for 10 days, which was confirmed by hematoxylin & eosin staining, A: osteoblasts, B: fibrous tissues
Figure 7A:
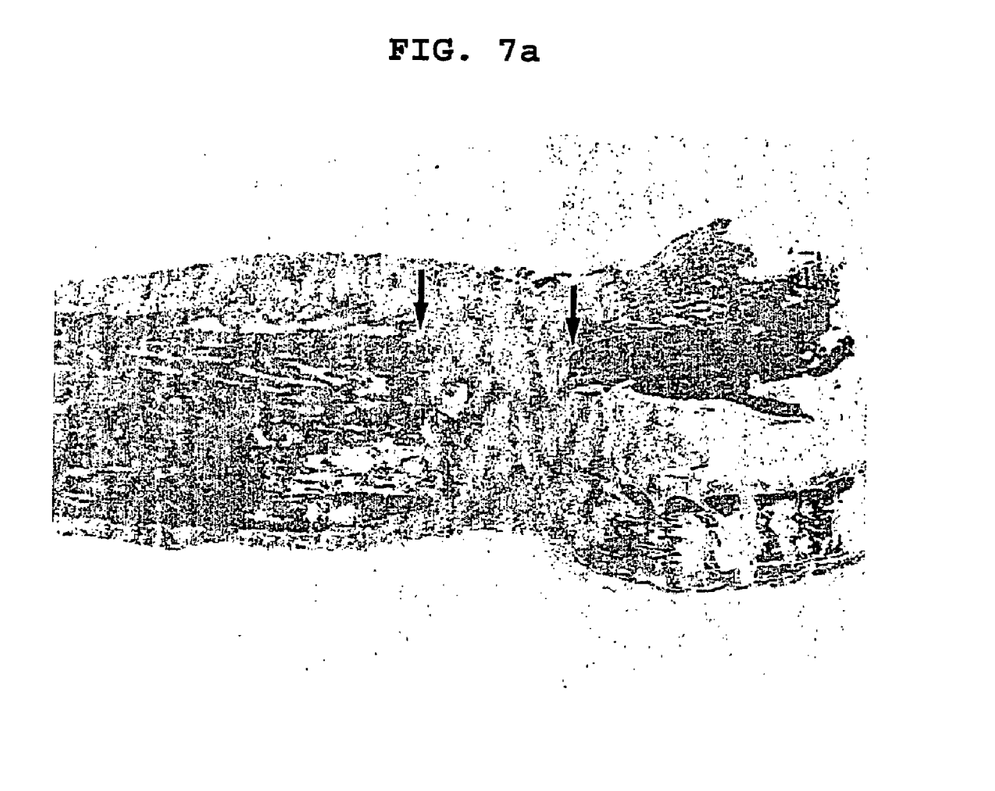
FIG. 7A is a photograph showing the histological section of a control group 2 3 weeks after bone extension, particularly the group was injected with only carboxymethylcellulose and was induced to have 2 mm extension per day for 5 days, Arrows: the first cutting parts
Figure 7B:
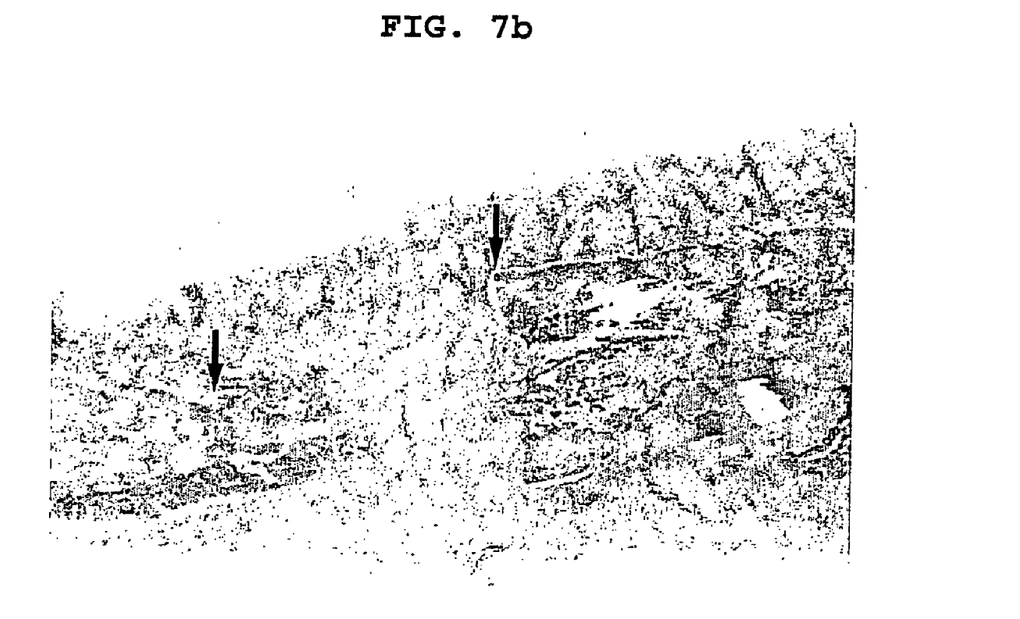
FIG. 7B is a photograph showing the histological section of a control group 2 6 weeks after bone extension, particularly the group was injected with only carboxymethylcellulose and was induced to have 2 mm extension per day for 5 days, Arrows: the first cutting parts
Figure 7C:
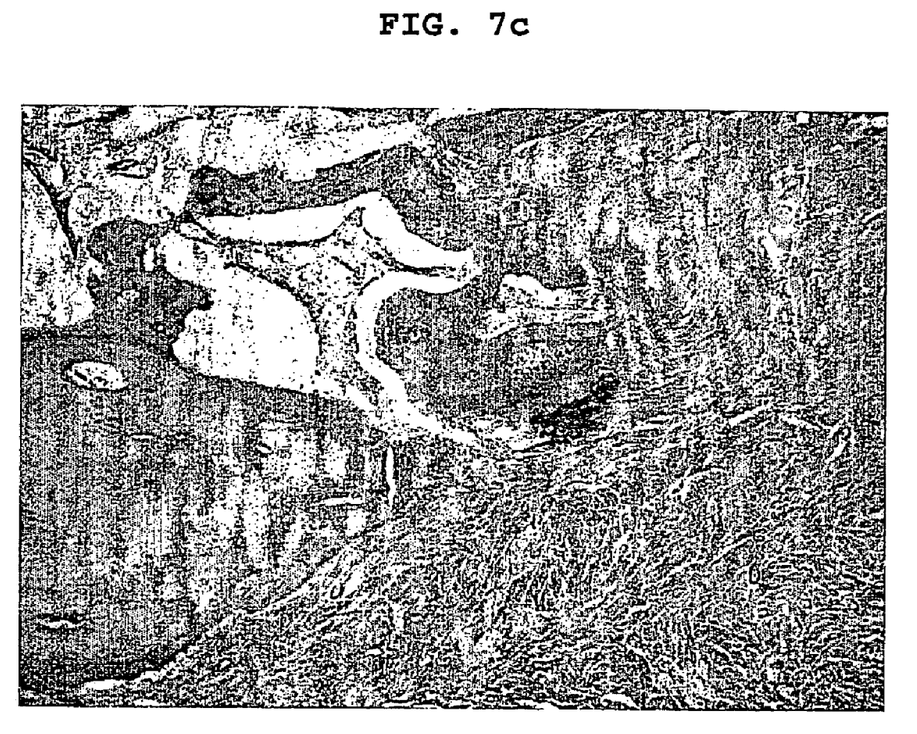
FIG. 7C is a photograph showing the new bone-formation at the edge of bone extension region in a control group 2 injected carboxymethylcellulose only and induced to have 2 mm extension per day for 5 days, which was confirmed by hematoxylin & eosin staining, A: osteoblasts, B: fibrous tissues
Figure 8C:
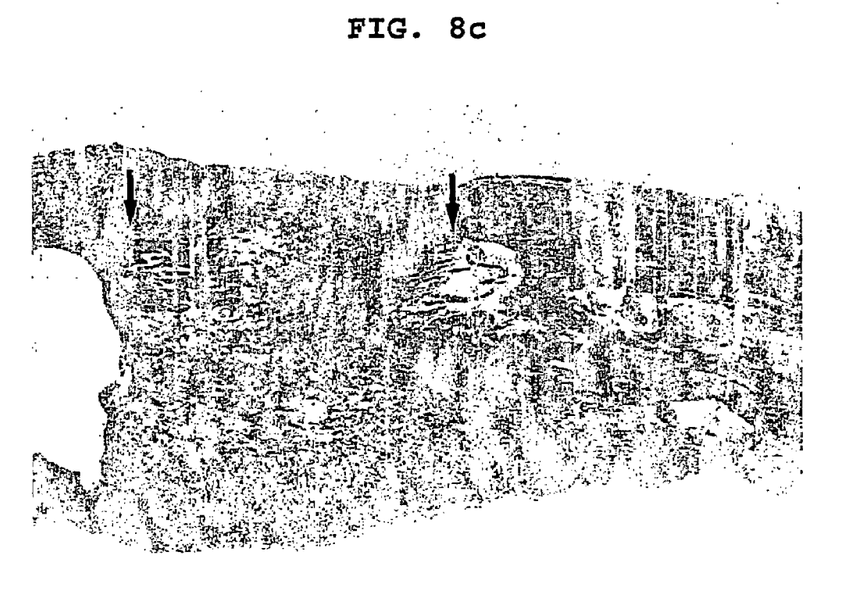
FIG. 8C is a photograph showing the histological section of a calcium sulfate group 1 6 weeks after bone extension, particularly the group was injected with the composition of the present invention and was induced to have 1 mm extension per day for 10 days, Arrows: the first cutting parts
Figure 8D:
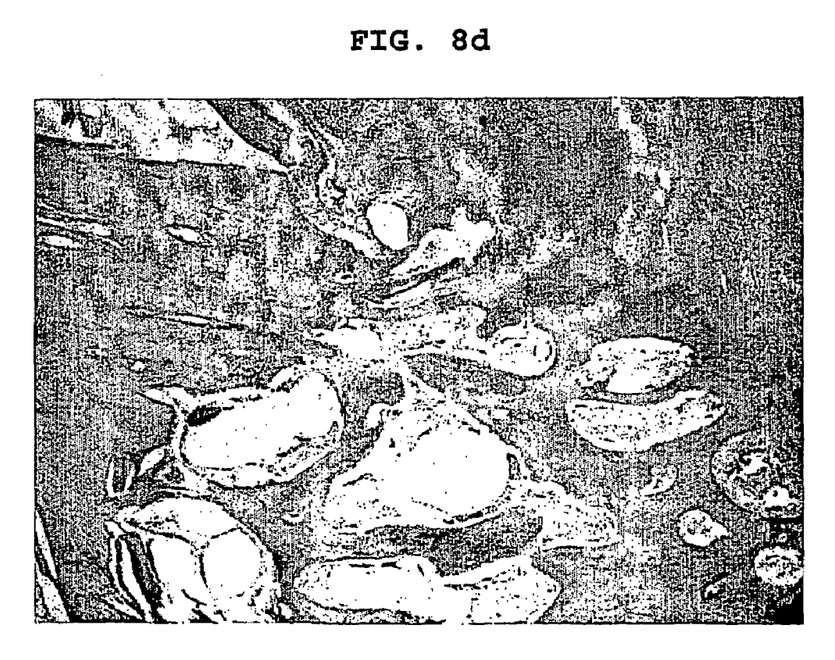
FIG. 8D is a photograph showing the new bone-formation over the whole extended region, which was confirmed by hematoxylin & eosin staining with the histological section of FIG. 8C.
Figure 9A:
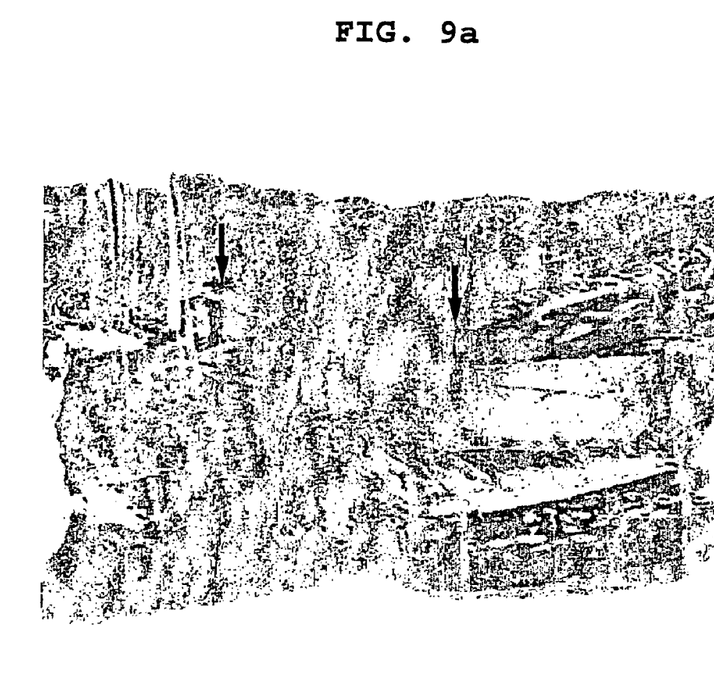
FIG. 9A is a photograph showing the histological section of a calcium sulfate group 2 3 weeks after bone extension, particularly the group was injected with the composition of the present invention and was induced to have 2 mm extension per day for 5 days, Arrows: the first cutting parts
Figure 9B:
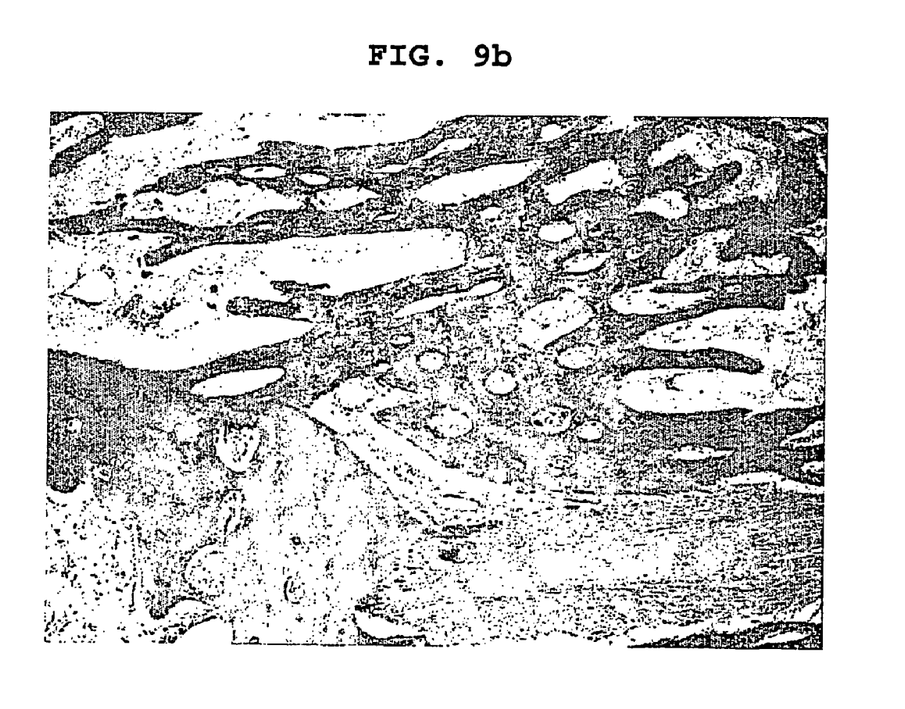
FIG. 9B is a photograph showing that bone-formation was begun from the edge and fibrous interzone was connected with the extended area, which was confirmed by hematoxylin & eosin staining with the histological section of FIG. 9A.
Figure 9C:
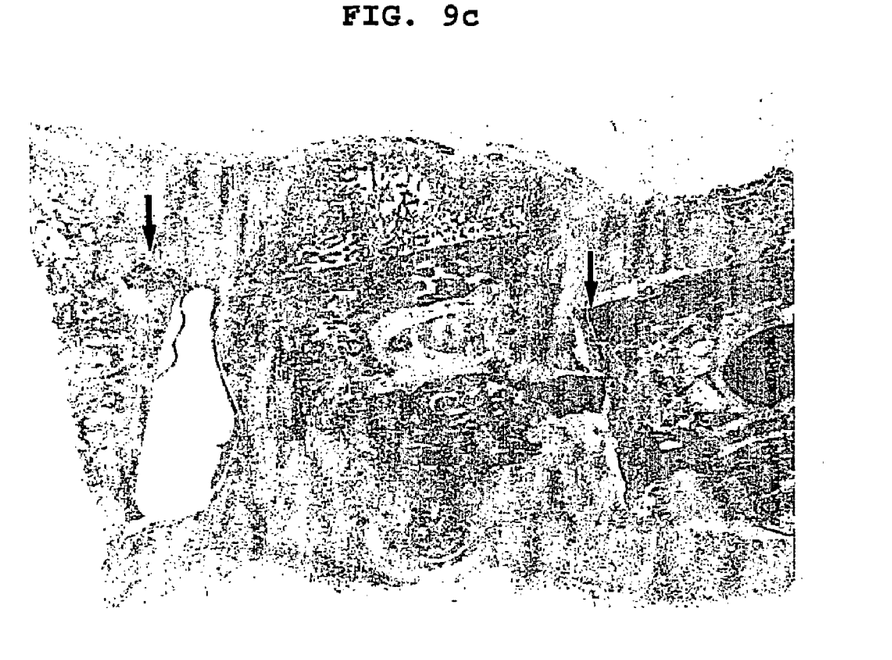
FIG. 9C is a photograph showing the histological section of a calcium sulfate group 2 6 weeks after bone extension, particularly the group was injected with the composition of the present invention and was induced to have 2 mm extension per day for 5 days, Arrows: the first cutting parts
Figure 9D:
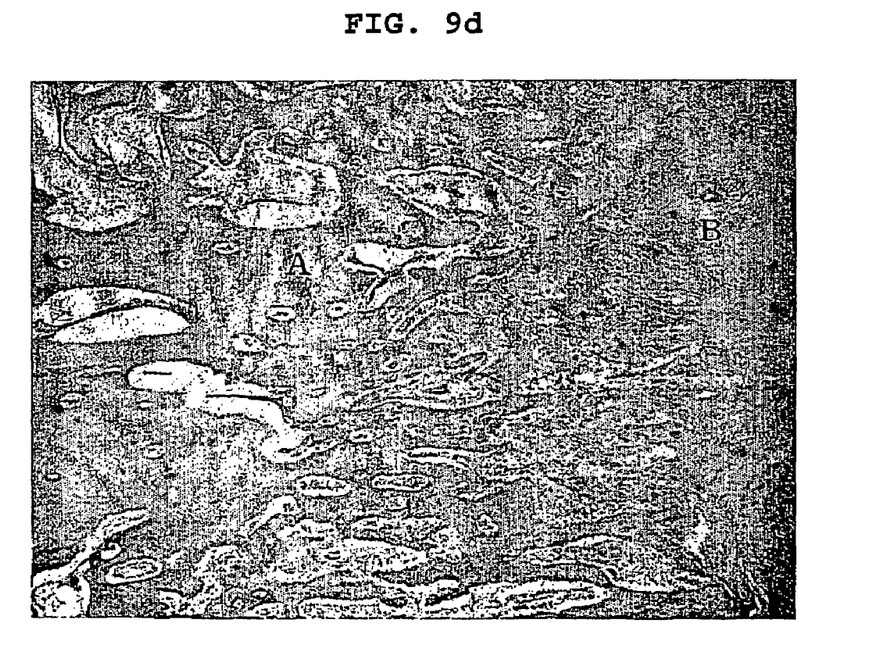
FIG. 9D is a photograph showing the new bone-formation in half of extended area, which was confirmed by hematoxylin & eosin staining with the histological section of FIG. 9C.

As a result, osteoblasts forming osteoid were partly found on the edge of the extended area and lots of fibrous tissues were seen in the center area in a control group 1 in the $3^{rd}$ week after extension (FIG. 6A). In the $6^{th}$ week after extension, newly formed bone was observed more than in the $3^{rd}$ week and the center of the extended area was filled with fibrous tissues (FIGS. 6B and 6C). In a control group 2, new bone-formation was partly observed in the extended area and most of the extended area was filled with fibrous tissues (FIG. 7). In a composition group 1, lots of active osteoblasts were seen over the edge and the center of the extended area and the areas were filled with newly formed bone and fibrous tissues in the $3^{rd}$ week after extension (FIGS. 8A and 8B). In the $6^{th}$ week after extension, the new bone formed throughout the whole extended area was almost similar to the normal cortical bone (FIGS. 8C and 8D). In a composition group 2, extended area was bridged by fibrous interzone and new bone-formation was observed along the edge in the $3^{rd}$ week after extension (FIGS. 9A and 9B). In the $6^{th}$ week, newly formed bone was observed around half of the extended area (FIGS. 9C and 9D).

INDUSTRIAL APPLICABILITY

As described hereinbefore, the gel type composition of the present invention induces new bone-formation, provides a normal bone-structure, prevents the growth of unnecessary connecting tissues and is suitable for human enough to be substituted for bone during the recovery process as well as induces the growth of blood vessels and bony osteogenesis cells in the early stage. Therefore, the composition of the present invention can be effectively used as a bone-filling material suitable for body.

What is claimed is:

1. A gel type bone-filling composition for stimulating bone-formation and bone-consolidation comprising
   1) 20~80 weight % of a mixture containing calcium sulfate, $CaCO_3$, $MgCO_3$, and $CaCO_3.MgCO_3$, wherein the mixture contains 98-99 weight % of calcium sulfate, 0.3-1 weight % of $CaCO_3$, 0.3-1 weight % of $MgCO_3$ and 0.5-1 weight % of $CaCO_3.MgCO_3$; and
   2) 80~20 weight % of a viscous biopolymer.

2. The bone-filling composition for stimulating bone-formation and bone-consolidation as set forth in claim 1, wherein the viscous biopolymer is selected from a group consisting of carboxymethylcellulose, hyaluronic acid, chitosan, cellulose ethers, cellulose esters, starches and polysaccharides.

3. The bone-filling composition for stimulating bone-formation and bone-consolidation as set forth in claim 2, wherein the viscous biopolymer is carboxymethylcellulose.

4. The bone-filling composition for stimulating bone-formation and bone-consolidation as set forth in claim 1, wherein the ratio of calcium sulfate to viscous biopolymer is 50:50.

5. The bone-filling composition for stimulating bone-formation and bone-consolidation as set forth in claim 1, wherein the calcium sulfate is $CaSO_4$ or $CaSO_4.H_2O$.

6. The bone-filling composition for stimulating bone-formation and bone-consolidation as set forth in claim 4, wherein the ratio of calcium sulfate to carboxymethylcellulose is 50:50.

* * * * *